(12) United States Patent
Muller et al.

(10) Patent No.: US 7,761,160 B2
(45) Date of Patent: *Jul. 20, 2010

(54) SYSTEM AND METHOD FOR DETERMINING ATRIOVENTICULAR PACING DELAY BASED ON ATRIAL REPOLARIZATION

(75) Inventors: David Muller, Sicklerville, NJ (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/622,139

(22) Filed: Nov. 19, 2009

(65) Prior Publication Data

US 2010/0069990 A1 Mar. 18, 2010

Related U.S. Application Data

(63) Continuation of application No. 11/366,930, filed on Mar. 1, 2006, now Pat. No. 7,643,878.

(51) Int. Cl.
*A61N 1/00* (2006.01)
(52) U.S. Cl. .................................................. 607/25
(58) Field of Classification Search ................ 607/25, 607/9
See application file for complete search history.

(56) References Cited

U.S. PATENT DOCUMENTS

| | | | |
|---|---|---|---|
| 6,594,523 B1 | 7/2003 | Levine | |
| 6,615,083 B2 | 9/2003 | Kupper | |
| 7,630,764 B2 * | 12/2009 | Ding et al. | 607/9 |
| 2003/0014083 A1 | 1/2003 | Kupper | |
| 2005/0137630 A1 | 6/2005 | Ding et al. | |

OTHER PUBLICATIONS

Worley, Seth J. et al., "Optimization of Cardiac Resynchronization: Left Atrial Electrograms Measured at Implant Eliminates the Need for Echo and Identifies Patients Where AV Optimization is not Possible," Journal of Cardiac Failure;10(4 Supp)—Abstract #160.
NonFinal Office Action, mailed Nov. 10, 2008—U.S. Appl. No. 11/366,930.
NonFinal Office Action, mailed May 8, 2009—U.S. Appl. No. 11/366,930.
Notice of Allowance, mailed Oct. 30, 3009—U.S. Appl. No. 11/366,930.

* cited by examiner

*Primary Examiner*—George Manuel
*Assistant Examiner*—Robert N Wieland

(57) ABSTRACT

Techniques are provided for estimating optimal atrioventricular pacing delay values for use in pacing the ventricles based on features of an intracardiac electrogram (IEGM) signal. Briefly, atrioventricular pacing delay pacing values are set based upon the location of atrial repolarization events within the IEGM. In one example, the end of an atrial repolarization is identified, then the interval from the atrial depolarization to the end of the atrial repolarization is measured. The atrioventricular pacing delay is then set by subtracting an offset value from that interval so as to time delivery of V-pulses prior the end of atrial repolarization. In this manner, atrioventricular pacing delay values are set based only IEGM signals and hence can be set to optimal/preferred values by the device itself without requiring surface electrocardiogram (EKG) signals and Doppler echocardiography or other cardiac performance monitoring techniques.

14 Claims, 8 Drawing Sheets

FIG. 4
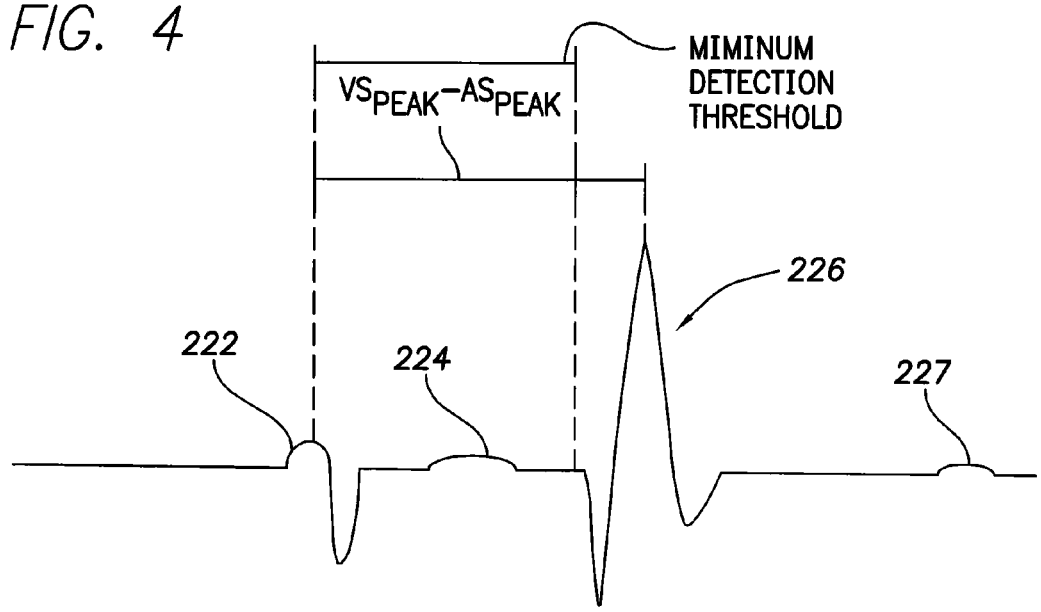
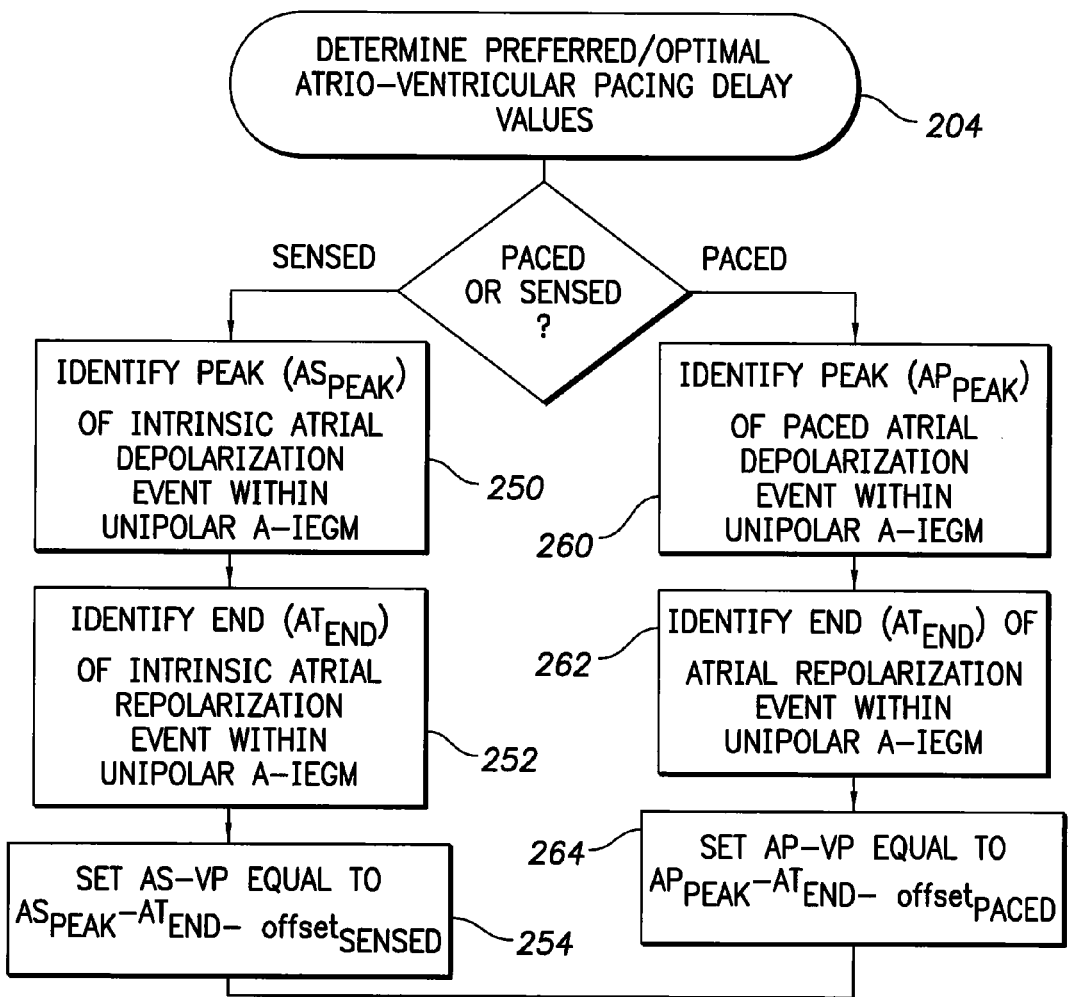
FIG. 5

SYSTEM AND METHOD FOR DETERMINING ATRIOVENTRICULAR PACING DELAY BASED ON ATRIAL REPOLARIZATION

CROSS REFERENCE TO RELATED APPLICATIONS

This application is a continuation of U.S. patent application Ser. No. 11/366,930, filed Mar. 1, 2006, now U.S. Pat. No. 7,643,878.

FIELD OF THE INVENTION

The invention generally relates to implantable cardiac stimulation devices for use in pacing the heart of a patient and in particular to techniques for determining optimal or preferred atrioventricular pacing delay times for individual patients based on intracardiac electrogram (IEGM) signals.

BACKGROUND OF THE INVENTION

A pacemaker is implantable cardiac stimulation device for implant within a patient that analyzes an IEGM to detect various arrhythmias such as an abnormally slow heart rate (bradycardia) or an abnormally fast heart rate (tachycardia) and delivers electrical pacing pulses to the heart in an effort to remedy the arrhythmias. An implantable cardioverter-defibrillator (ICD) additionally detects atrial fibrillation (AF) or ventricular fibrillation (VF) and delivers electrical shocks to terminate fibrillation.

For many patients, particularly those with congestive heart failure (CHF), it is desirable to identify a set of control parameters for controlling the operation of the pacemaker or ICD that will yield optimal cardiac performance (also referred to as hemodynamic performance). Cardiac performance is a measure of the overall effectiveness of the cardiac system of a patient and is typically represented in terms of stroke volume or cardiac output. Stroke volume is the amount of blood ejected from the left ventricle during systole in a forward direction. Cardiac output is the volume of blood pumped by the left ventricle per minute (or stroke volume times the heart rate). In view of the importance of maintaining optimal cardiac performance, especially for patients with compromised cardiac function, it would be desirable to provide improved techniques for use with pacemakers or ICDs or other implantable cardiac stimulation devices for identifying pacing control parameters that optimize cardiac performance, particularly to reduce the degree of heart failure and valvular regurgitation. It is to this end that aspects of the invention are generally directed.

A useful control parameter for optimizing cardiac performance is the atrioventricular pacing delay, referred to herein is the A-VP delay, which for dual chamber devices specifies the time delay between a paced or sensed atrial event and a paced ventricular event. Sensed events (i.e. intrinsic or native events) are also referred to as depolarization events as these events are representative of electrical depolarization of myocardial tissue. Paced events are also referred to herein as evoked responses. Paced events in the atria are triggered by A-pulses generated by the implantable device. Paced events in the ventricles are triggered by V-pulses also generated by the implantable device. Note that, herein, "A" is generally used to refer to atrial events, whether paced or sensed. "V" is used to generally refer to ventricular events, whether paced or sensed. In circumstances where it is necessary to distinguish between paced and sensed events, an "S" or "P" is appended. Hence, AS refers to a sensed atrial event, whereas AP refers to paced atrial event. VS refers to a sensed ventricular event, whereas VP refers to a paced ventricular event. Thus, A-VP generally represents the delay between either a paced or sensed atrial event and a paced ventricular event. AS-VP specifically refers to the delay between a sensed atrial event and the paced ventricular event; whereas AP-VP specifically refers to the delay between a paced atrial event and the paced ventricular event.

In addition, where appropriate, an "L" or "R" subscript is employed herein to distinguish between the left and right chambers of the heart. For example, $AP_R$ refers to a paced event in the right atrium. $VS_R$ refers to a sensed event in the right ventricle. Hence, $AP_R$–$VS_R$ represents the delay between a paced event in the right atrium and a sensed event in the right ventricle. Also, where appropriate, a "PEAK" or "END" subscript is employed herein to distinguish between the peak and end of a given event. For example, $AS_{PEAK}$ represents the peak of a sensed atrial event; whereas $AS_{END}$ represents the end of the sensed atrial event. The term "intrinsic delay", as used herein, refers to the delay between a paced or sensed event in one chamber and a subsequent sensed depolarization in another chamber. For example, an "intrinsic atrioventricular delay" refers to the delay between a paced or sensed atrial event and a subsequent sensed ventricular event, e.g. an AS-VS or AP-VS delay. Also, a "T" is used herein to identify repolarization events. For example, AT refers to an atrial repolarization; whereas VT refers to a ventricular repolarization. Note that the A, V and T events, whether paced or sensed, are all features of the IEGM signal sensed and recorded by the implantable device. The features are also observable in surface electrocardiogram (EKG) signals obtained via leads temporarily affixed to the chest of the patient. The corresponding feature of an AS event observed within the surface EKG is referred to as a P-wave. The corresponding feature of a VS event observed within the surface EKG is referred to as an R-wave. The corresponding feature of a repolarization event observed within the surface EKG is referred to as a T-wave. Finally, note that the VS event of the IEGM is also often referred to as a QRS complex.

In normal patients, the electrical conduction through the atrioventricular node is intact, and the body automatically adjusts the intrinsic atrioventricular delay (AS-V) via the circulating hormones and the autonomic nervous system according to its physiologic state. It is well known, for example, that in normal patients the intrinsic atrioventricular delay shortens with increasing heart rate associated with a physiologic stress such as exercise. For patients with abnormal atrioventricular node conduction or complete heart block, a pacemaker can control the A-VP delay (i.e. either the AS-VP delay, the AP-VP delay or both) by delivering a ventricular pacing pulse at a software-controlled delay after an atrial pace or atrial sensed event. Since the optimum A-VP delay varies from person to person, this parameter should be optimized on an individual basis.

Conventionally, the physician attempts to program the A-VP delay (or other parameters) for a given patient by using an external programmer to control the device implanted within the patient to cycle through a set of different A-VP delay values. For each value, the implanted device paces the heart of the patient for at least a few minutes to permit hemodynamic equilibration, then the physician records a measure of the resulting cardiac performance, measured, for example, using Doppler echocardiography. The A-VP delay value that yields the best cardiac performance is then selected and programmed into the device. However, this is a time consuming and potentially expensive procedure. As a result, some physicians do not bother to optimize A-VP delay in many of their patients. Rather, A-VP delay is merely set to a default value and is adjusted only if the patient does not respond well to pacing therapy or complains that they do not feel well.

Hence, many patients are not paced at their particular optimal A-VP delay value and thus do not obtain the maximal potential benefit from the improved cardiac performance that could otherwise be gained. Moreover, even in circumstances wherein A-VP delay is optimized by the physician using, for example, Doppler echocardiography, the time and associated costs are significant. In addition, the optimal A-VP delay for a particular patient may change with time due to, for example, progression or regression in CHF, changes in medications, and/or changes in overall fitness. However, with conventional optimization techniques, the A-VP delay is re-optimized, if at all, only during specially scheduled follow-up sessions with the physician to allow access to the noninvasive testing equipment such as Doppler-echocardiography, which sessions may be months or perhaps years apart.

Accordingly, it is would be highly desirable to provide improved techniques for more easily and reliably determining optimal or otherwise preferred A-VP delay values for a particular patient. Preferably, such techniques would be designed so as to be performed by the implantable device itself using only IEGM data, so that Doppler echocardiography or other expensive and time consuming cardiac performance monitoring techniques are no longer required. This permits the optimal A-VP delay to be frequently and automatically updated so as to respond to changes within the patient.

Many of these needs have been met by techniques set forth in U.S. patent application Ser. No. 10/928,586, of Bruhns et al., entitled "System and Method for Determining Optimal Atrioventricular Delay based on Intrinsic Conduction Delays", filed Aug. 27, 2004, which is incorporated by reference herein. Briefly, techniques are provided therein where both the intrinsic inter-atrial conduction delay and the intrinsic atrioventricular conduction delay are determined for the patient and then preferred A-VP delay values are derived therefrom. In one example, the technique uses only IEGM signals and surface EKG signals and hence can be performed by an external programmer without requiring Doppler echocardiography or other cardiac performance monitoring techniques. In another example, wherein the implanted device is equipped with a coronary sinus lead, the technique uses only IEGM signals and hence can be performed by the device itself.

Although the techniques of Bruhns et al. are effective, it would be desirable to provide alternative techniques for determining optimal or otherwise preferred A-VP delay values for a patient, particularly techniques that do not require the use of a surface EKG, and it is to that end that the present invention is more specifically directed.

SUMMARY

In accordance with one illustrative embodiment, techniques are provided for determining atrioventricular pacing delay values (i.e. A-VP values) for use in delivering cardiac pacing therapy to the heart of a patient in which an implantable cardiac stimulation device is implanted. Broadly, an atrial repolarization event is detected within an electrical cardiac signal and then A-VP values are determined based on the atrial repolarization event. By basing the determination of the A-VP delay values on atrial repolarization events, pacing delay values can be readily determined based only on IEGM signals so that surface EKG signals need not be employed and cardiac performance monitoring techniques, such as Doppler echocardiography, are not required.

Preferably, separate A-VP delay values are determined for use with paced atrial events and sensed atrial events, i.e. separate values are determined for AS-VP pacing and for AP-VP pacing. In one example, the AS-VP delay is set relative to the end of the atrial repolarization event ($AT_{END}$) by determining the duration of an $AS_{PEAK}$–$AT_{END}$ interval, then subtracting a predetermined offset value ($offset_{SENSED}$) suitable for use with sensed (i.e. intrinsic) atrial events. (Alternatively, rather than timing the interval beginning with $AS_{PEAK}$, the interval may be timed beginning at the point when the AS is first detected.) The AS-VP delay is then used to time the delivery of V-pulses following detection of intrinsic atrial depolarization events (i.e. P-waves). The AP-VP delay is also set relative to the end of the atrial repolarization event ($AT_{END}$) by determining the duration of an $AP_{PEAK}$–$AT_{END}$ interval, then subtracting a different predetermined offset value ($offset_{PACED}$) suitable for use with paced atrial events. (Alternatively, rather than timing the interval beginning with $AP_{PEAK}$, the interval may be timed beginning at the point at which the A-pulse is delivered.) The AP-VP delay is then used to time the delivery of V-pulses following paced atrial depolarization events (i.e. A-pulses). In one specific example, $offset_{PACED}$ is set to 10 ms and $offset_{SENSED}$ is set to 20 ms.

It is believed that the AS-VP and AP-VP delay values calculated in this manner approximate optimal delay values in that the values tend to maximize ventricular filling so as to maximize cardiac performance. However, even if the delay values differ from true optimal values, they nevertheless represent preferred delay values likely to improve ventricular filling. Preferably, delay values for both AS-VP and AP-VP are calculated and used. Alternatively, a preferred AS-VP value could be calculated and used in conjunction with an AP-VP value selected using otherwise conventional techniques, or vice versa.

By calculating the AS-VP and AP-VP delay values by subtracting offsets from the measured intervals (i.e. $AS_{PEAK}$–$AT_{END}$, and $AP_{PEAK}$–$AT_{END}$, respectively), the V-pulses are thereby timed to be delivered before the end of subsequent atrial repolarization events. Hence, the ends of the atrial repolarization events are no longer detectable within the IEGM. Preferably, ventricular pacing is periodically suspended to again allow for detection of the ends of atrial repolarization events so that the AS-VP and AP-VP delay values can be reset if needed. Also preferably, steps are performed to verify that the intrinsic atrioventricular delay of the patient (i.e. the AS-VS and AP-VS delays) are sufficiently long so that $AT_{END}$ can be reliably detected. In one example, ventricular pacing is suspended to allow detection of the AS-VS and AP-VS delays, which are then compared against minimum atrial repolarization detection threshold values. So long as the AS-VS and AP-VS delays exceed their respective threshold values, there is a sufficient interval of time to allow the ends of atrial repolarization events to be detected so as to permit optimizing the AS-VP and AP-VP delay values based on the timing of those ends. Otherwise, alternative optimization techniques are preferably employed for setting the AS-VP and AP-VP delay values, which do not rely on detection of the ends of the atrial repolarization events.

Depending upon the implementation and the circumstances, the AS-VP and AP-VP delay values may be adjusted based on the intrinsic heart rate of the patient or on the current pacing rate. In one example, adjustment of the AS-VP delay value is performed by applying a scaling factor ($\beta_{SENSED}$) to an AS-VP delay value measured at patient rest rate, where the scaling factor is $\beta_{SENSED}$=(Current Intrinsic Heart Rate)/(Patient Rest Rate). Adjustment of the AP-VP delay value is performed by applying a scaling factor ($\beta_{PACED}$ to an AP-VP delay value measured at a base pacing rate, where the scaling factor is $\beta_{PACED}$=(Current Pacing Heart Rate)/(Base Pacing Rate).

BRIEF DESCRIPTION OF THE DRAWINGS

The above and further features, advantages and benefits of the invention will be apparent upon consideration of the present description taken in conjunction with the accompanying drawings, in which:

FIG. 4 is a graph providing a stylized representation of an IEGM signal, particularly illustrating a threshold used by the technique of FIG. 3 to verify that the ends of atrial repolarization events can be detected;

FIG. 5 is a flow chart illustrating an exemplary technique for determining separate atrioventricular delay values for paced and sensed events for use with the technique of FIG. 2;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Techniques for Determining A-VP Delay Values

Figure 1:
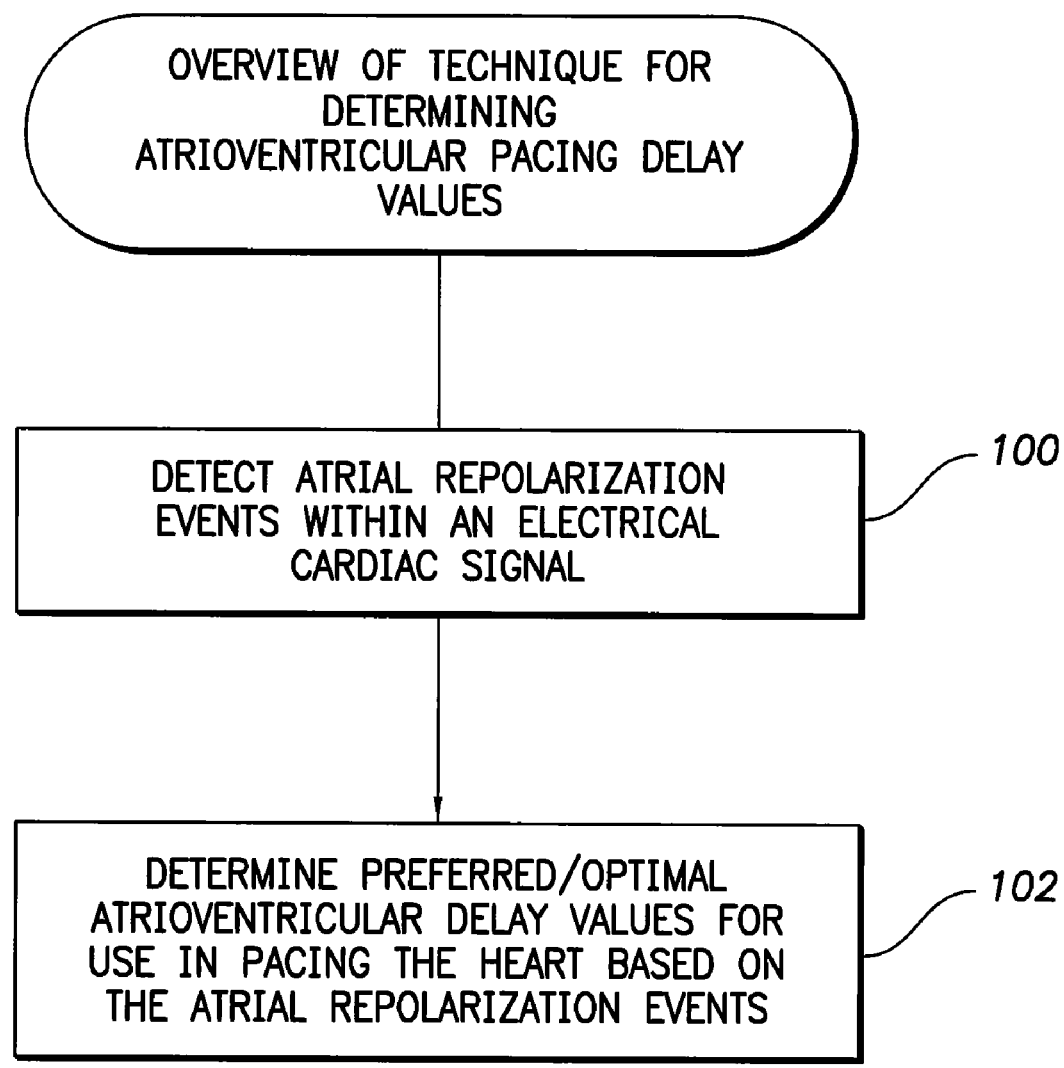
FIG. 1 is a flow chart providing an overview of techniques provided in accordance with the invention for identifying preferred A-VP delay values based on atrial repolarization (AT) events.

Within FIG. 1, at step 100, atrial repolarization events are detected within an electrical cardiac signal, such as an IEGM signal, sensed within the heart of a patient by an implantable medical device implanted within the patient. Atrial repolarization events, which represent the electrical repolarization of myocardial tissue subsequent to a previous depolarization of the tissue, are also referred to herein as atrial T-waves. Then, at step 102, preferred atrioventricular pacing delay values (i.e. A-VP values) are determined by the implantable device based on the atrial repolarization events for use in pacing the heart of the patient. By basing the determination of the A-VP delay values, in part, on atrial repolarization events, preferred or optimal A-VP delay values can be readily determined by the implantable device itself without requiring complicated conventional techniques such as the use of Doppler echocardiography and the like and without requiring the use of surface EKGs, and hence costs are reduced. Moreover, since the determination is performed by the implanted device itself, the preferred or optimal A-VP delay values can thereby be recalculated as often as needed, based upon newly sensed IEGM signals, to update the A-VP delay values to maintain them at preferred or optimal values. Hence, the patient benefits from improved cardiac performance.

Atrial Repolarization End-Based Example

Figure 2:
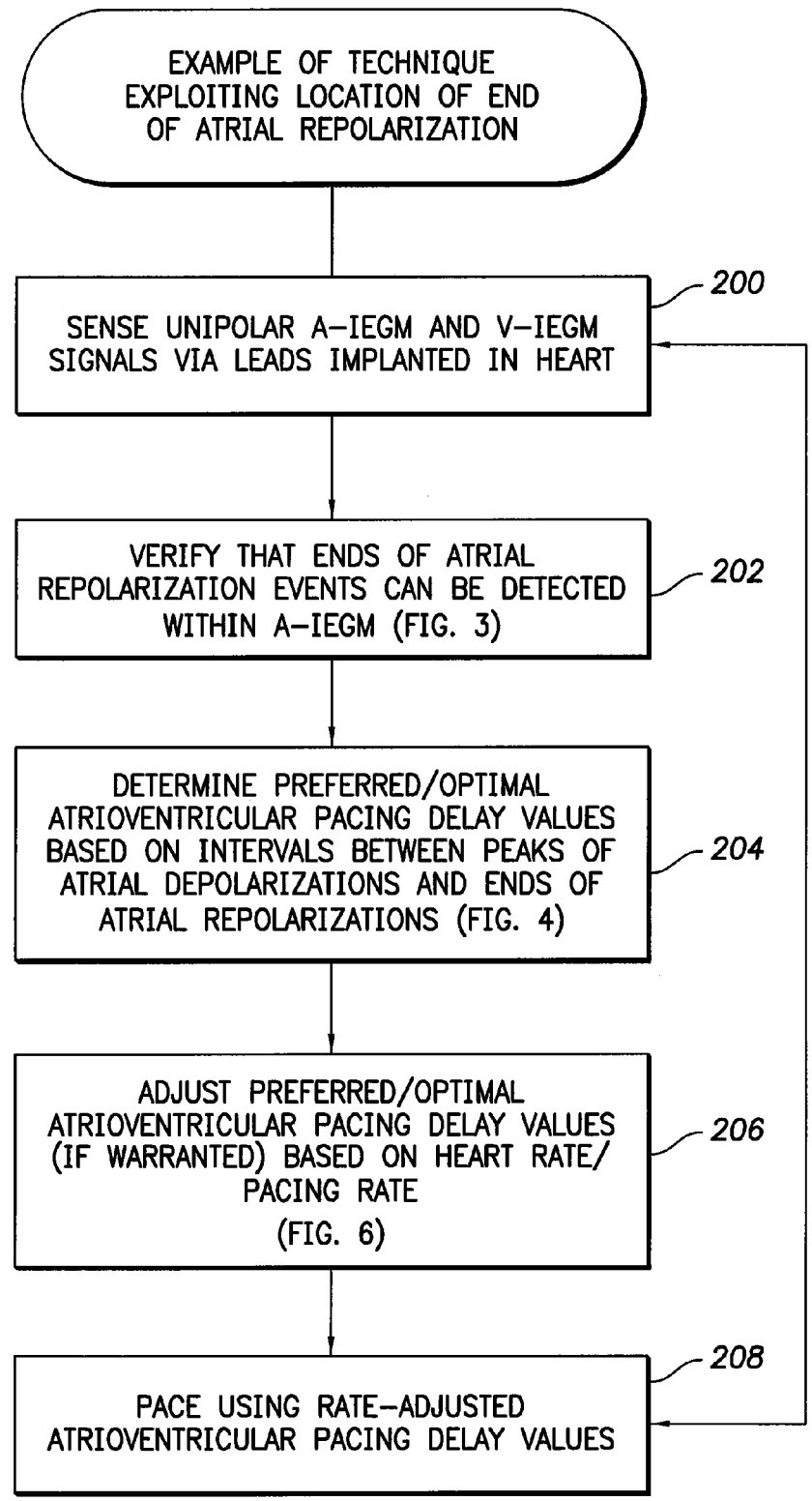
FIG. 2 is a flow chart illustrating an exemplary implementation of the technique of FIG. 1 wherein ends of atrial repolarization events are used to determine preferred A-VP delay values.

Referring now to FIG. 2, an exemplary technique will now be described that determines the optimal/preferred A-VP delay values based, in part, on the ends of the atrial repolarization events. Beginning at step 200, the implanted device senses unipolar atrial and ventricular IEGM signals (i.e. A-IEGM and V-IEGM signals) via leads implanted in the heart. By "unipolar", it is meant that the housing of the implanted device is used as a return electrode in combination with a sensing electrode implanted within the heart. Preferably, a lead implanted within the right atrium is used to sense the unipolar A-IEGM signal; whereas a lead implanted within the right ventricle is used to sense the unipolar V-IEGM signal.

At step 202, the implanted device verifies that the ends of atrial repolarization events can be detected within the unipolar A-IEGM, i.e. that the intrinsic atrioventricular delay within the heart of the patient is sufficiently long such that the $AT_{END}$ is not obscured by intrinsic ventricular depolarization events. Verification may be accomplished using a technique to be described below with reference to FIGS. 3-4. If the ends of atrial repolarization events cannot be detected within the unipolar A-IEGM signal (either due to short intrinsic atrioventricular delays or for any other reason), then alternative atrioventricular pacing delay optimization techniques may instead be used to set the A-VP delay values. Suitable alternative techniques include, for example, techniques set forth in the above-referenced patent application of Bruhns et al. Alternatively, A-VP delay values obtained via the invention at another heart rate (such as a base/rest rate) may be rate adjusted, then applied at the current rate.

Figure 6:
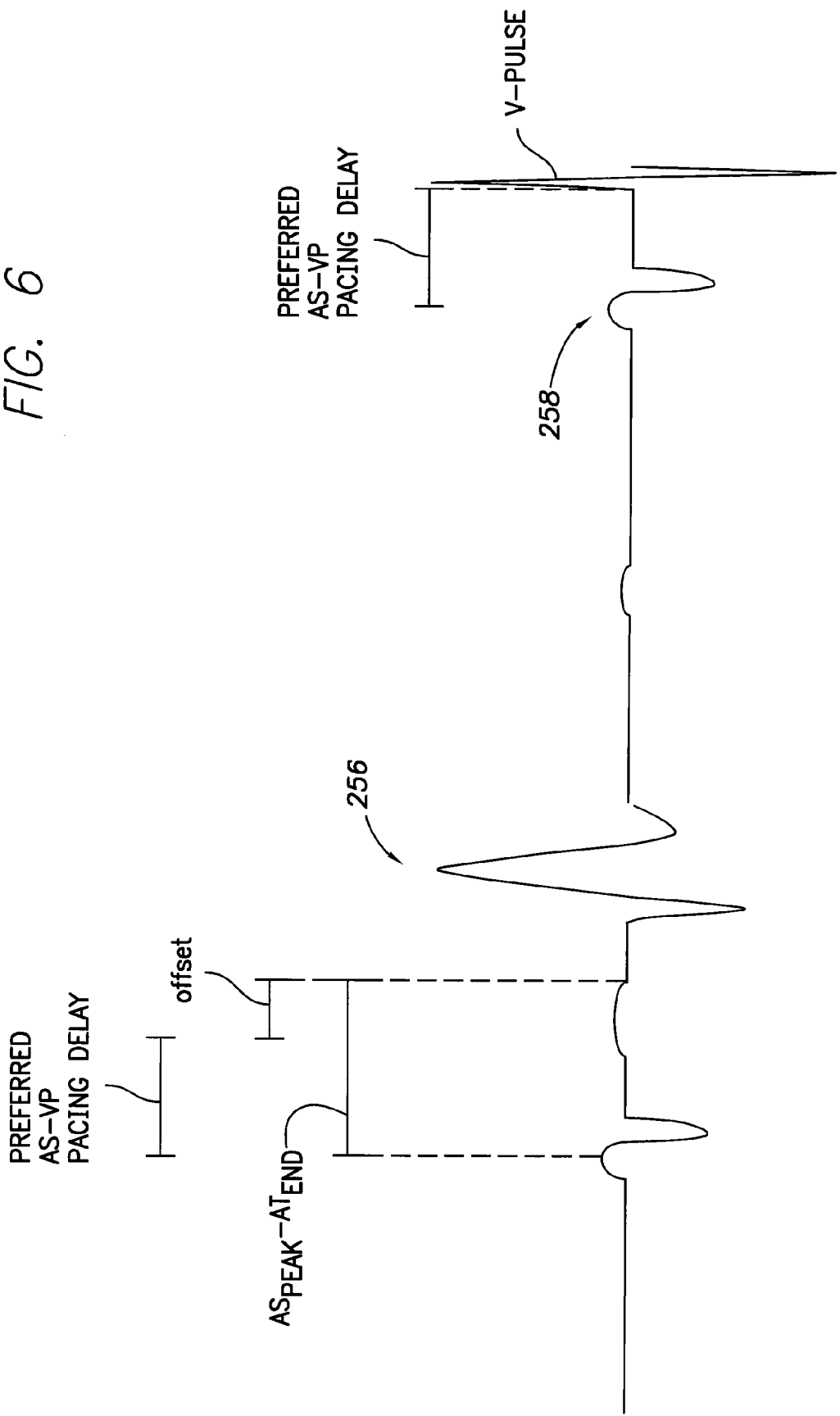
FIG. 6 is a graph providing a stylized representation of an IEGM signal, particularly illustrating an offset used by the technique of FIG. 5 for setting atrioventricular delay values relative to the ends of atrial repolarization events.

Assuming that the ends of the atrial repolarization events can be detected, then, at step 204, the implanted device determines preferred atrioventricular pacing delay (A-VP) values based on intervals between the peaks of atrial depolarization events and the ends of the atrial repolarization events, using techniques described below with reference to FIGS. 5-6. Preferably, separate atrioventricular pacing delay values are determined for use with sensed and paced atrial events, i.e. both AS-VP and AP-VP values are determined. If the preferred AS-VP and AP-VP delay values are to be used at a heart rate significantly different from the rate at which the delay values were calculated, then the delay values are preferably adjusted, at step 206, based upon the current heart rate or pacing rate using techniques described below with reference to FIG. 7. Finally, at step 208, the implanted device paces the ventricles of the patient using the rate-adjusted AS-VP and AP-VP delay values.

Figure 3:
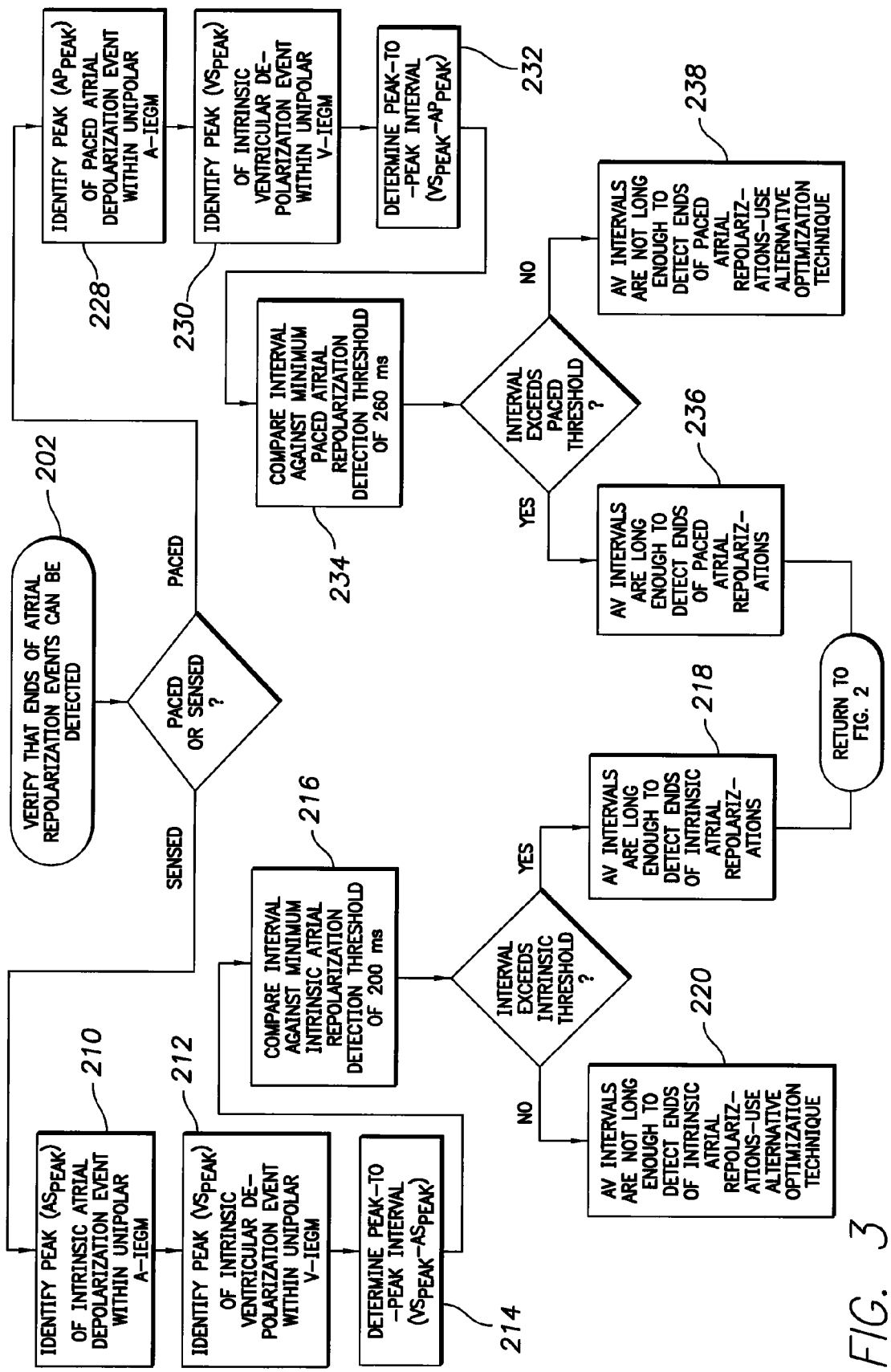
FIG. 3 is a flow chart illustrating an exemplary technique for verifying that the ends of the atrial repolarization events can be detected for use with the technique of FIG. 2.

Turning now to FIGS. 3-4, the verification technique of step 202 of FIG. 2 will now be described in detail. Processing depends upon whether atrial events are sensed or paced, i.e. processing depends upon whether the implanted device is currently allowing the atria to beat on their own or whether A-pulses are being delivered to the atria via the implanted leads. Referring first to sensed events, beginning at step 210, the implanted device detects the peak of an intrinsic atrial depolarization within the A-IEGM signal (i.e. $AS_{PEAK}$.) At step 212, the implanted device then detects the peak of the subsequent intrinsic ventricular depolarization event within the V-IEGM signal (i.e. $VS_{PEAK}$.) Alternatively, the A-IEGM signal may be used to detect both the atrial depolarization peak and the ventricular depolarization peak. Otherwise conventional techniques may be employed for detecting depolarization events within electrical cardiac signals and for identifying the peaks of those events.

At step 214, the implanted device then determines the intrinsic atrioventricular delay interval for sensed atrial events by calculating $VS_{PEAK}-AS_{PEAK}$ The interval is then compared, at step 216, against a minimum intrinsic atrial repolarization detection threshold that may be set, for example, to 200 milliseconds (ms). If the interval exceeds the threshold, then the intrinsic atrioventricular delay of the patient is sufficiently long to allow detection of the ends of intrinsic atrial repolarization events, step 218, and processing returns to FIG. 2 for determination of preferred/optimal AS-VP delay values based upon the ends of the atrial repolarization events. If, however, the interval does not exceed the threshold, then the intrinsic atrioventricular delay of the patient is not sufficiently long to allow for detection of the ends of the intrinsic atrial repolarization events, step 220. Accordingly, alternative optimization techniques are preferably employed to set the AS-VP delay, or the AS-VP delay is set to a default value.

Also, rather than detect the peak of the sensed atrial depolarization event at step 210, the device can instead use the time at which the atrial depolarization is first detected by the pacer/ICD. (Typically, an sensed atrial event is detected by comparing the A-IEGM signal against a detection threshold.) The intrinsic atrioventricular delay for sensed atrial events is then calculating as $VS_{PEAK}$-A-detected. This interval is then compared against a suitable detection threshold, which may differ from the 200 ms detection threshold used when measuring the intrinsic atrioventricular delay peak-to-peak.

The minimum detection threshold is illustrated in FIG. 4, which provides a stylized representation of an exemplary heartbeat of the patient observed within an A-IEGM signal, particularly illustrating an atrial depolarization event (i.e. AS) 222, an atrial repolarization event (i.e. AT) 224, a ventricular depolarization event (i.e. VS or QRS-complex) 226, and a ventricular T-wave 227 (i.e. VT). As can be seen, the QRS-complex does not begin until well after the end of the atrial T-wave and hence does not obscure the end of the atrial T-wave. This is verified by the implanted device by comparing the duration of the peak-to-peak interval (i.e. $VS_{PEAK}-AS_{PEAK}$) against the minimum detection threshold for use with sensed atrial events. If the peak-to-peak interval were instead less than the threshold, then portions of the QRS-complex might obscure the end of atrial repolarization event, preventing its detection.

Note that, when the intrinsic atrioventricular delay is measured peak-to-peak as in FIG. 4, care must be taken in setting the minimum detection threshold to account for those portions of the QRS complex preceding the peak of the QRS-complex. Otherwise, the measured intrinsic atrioventricular delay might exceed the minimum threshold, even though initial portions of the QRS-complex might obscure the end of atrial repolarization events. The exemplary threshold value noted above of 200 ms is typically sufficient to take this factor into account. Depending upon the implementation, the detection threshold is reprogrammable by the physician using an external programmer so that the physician can ensure that the detection threshold is set to a proper value for use with each particular patient. Alternatively, the intrinsic atrioventricular delay could be measured based on the start of the QRS-complex, rather than its peak. However, it is easier and more reliable to detect the peak of an event than to detect start of the event and so, in the preferred implementation of the invention, the intrinsic atrioventricular delay is measured peak-to-peak.

Also note that, within a given electrical event, one or more peaks can be identified. Within the example FIG. 4, the peak of the atrial depolarization event is identified as the first maxima within the event which, in the example, has a positive value (relative to a baseline signal level.) A second maxima occurs within the atrial depolarization event which, in the example, has a negative value. The second maxima has a larger absolute value than the first maxima. If desired, the second maxima could instead be used to define the peak of atrial depolarization event, with the detection threshold set accordingly. In general, any of a variety of markers may be used within the IEGM signals to measure values representative of the intrinsic atrioventricular delay of the patient for use in comparing against one or more thresholds to verify that the end of the atrial repolarization can be reliably detected.

Returning to FIG. 3, the processing steps for use with paced atrial events will now briefly be summarized. Beginning at step 228, the implanted device detects the peak of a paced atrial depolarization within the A-IEGM signal, i.e. the device detects the peak of the evoked response triggered in the atria by an A-pulse. The peak of the paced atrial depolarization as sensed within the atria is referred to herein as $AP_{PEAK}$. At step 230, the implanted device detects the peak of the subsequent intrinsic ventricular depolarization event within the V-IEGM signal. Alternatively, the A-IEGM signal may again be used to detect both the atrial depolarization peak and the ventricular depolarization peak. At step 232, the implanted device then determines the intrinsic atrioventricular delay interval for paced atrial events by calculating $VS_{PEAK}-AP_{PEAK}$. The duration of this interval is then compared, at step 234, against a minimum paced atrial repolarization detection threshold set, for example, to 260 milliseconds (ms). If the interval exceeds the minimum threshold, then the intrinsic atrioventricular delay of the patient is sufficiently long to allow detection of the ends of intrinsic atrial repolarization events arising following A-pulses, step 236, and processing returns to FIG. 2 for determination of preferred AP-VP delay values based upon the ends of the atrial repolarization events. If, however, the interval does not exceed the threshold, then the intrinsic atrioventricular delay of the patient is not sufficiently long to allow for detection of the ends of the paced atrial repolarization events, step 238. Alternative optimization techniques are then preferably employed to set the AP-VP delay, or the AP-VP delay is set to a default value.

Alternatively, rather than detect the peak of the paced atrial depolarization event at step 228, the device can simply record the time at which the A-pulse is delivered. The intrinsic atrioventricular delay for paced atrial events is then calculating as $VS_{PEAK}$-A-pulse. This interval is then compared against a suitable detection threshold, which may differ from the 260 ms detection threshold used when measuring the intrinsic atrioventricular delay peak-to-peak. Also, as with atrial sensed events, rather than measuring the intrinsic atrioventricular delay interval based upon the peak of the QRS-complex, the interval may instead be measured based on the start of the QRS-complex, though the peak is preferred for ease and reliability of detection. Also, although not shown in FIG. 3, the intrinsic atrioventricular delay is preferably measured for each of a plurality of heartbeats, with the values then averaged together before comparison against the minimum threshold values. This is preferred so as to prevent a single anomalous measurement of the intrinsic atrioventricular delay from activating or deactivating the atrial repolarization-based AV optimization techniques of the invention.

Turning to the FIG. 5, an exemplary technique for determining preferred/optimal atrioventricular pacing delay values for use at step 204 of FIG. 2 will now be described. Again, processing depends on whether atrial events are sensed or paced. Referring first to sensed events, beginning at step 250, the implantable device identifies the peak of an intrinsic atrial depolarization event ($AS_{PEAK}$) within the unipolar A-IEGM. At step 252, the end of the subsequent atrial repolarization event ($AT_{END}$) is then identified within the unipolar A-IEGM. In one example, a detection window is specified within the A-IEGM signal beginning 100 ms following the peak of the atrial depolarization event and extending to the end of the intrinsic atrioventricular delay measured at step 214 of FIG. 3. The implanted device first detects the atrial T-wave within that window, then identifies the end of the atrial T-wave. The end of the T-wave may be defined as the point at which the slope of the IEGM signal becomes substantially flat. Otherwise conventional techniques applicable to detecting the ends of ventricular T-waves typically may be employed for detecting the end of an atrial T-wave. Also, techniques set forth in the above-identified in patent application of Bruhns et al. may be adapted for use in detecting the end point of an atrial T-wave. See, also, end-point detection techniques set forth in U.S. patent application Ser. No. 10/603,398, entitled "System And Method For Detecting Cardiac Ischemia Based On T-Waves Using An Implantable Medical Device", of Min et al., filed Jun. 24, 2003, which is incorporated by reference herein.

At step 254, the preferred/optimal AS-VP delay is then determined by calculating:

$$AS\text{-}VP = AS_{PEAK} - AT_{END} - \text{offset}_{SENSED}$$

where $\text{offset}_{SENSED}$ is a predetermined offset value set, for example, within the range of 15 to 25 ms and, in one specific example, set to 20 ms. Otherwise routine experimentation may be performed for determining optimal values for offset-$_{SENSED}$ that result in optimization of cardiac output and/or ventricular filling (or the least result in an improvement therein.)

The preferred/optimal AS-VP delay value is then applied following subsequent sensed atrial events to determine the time for delivering V-pulses to the ventricles. This is illustrated in FIG. 6, which provides a stylized representation of a portion of electrical cardiac signal. During a first heartbeat 256, wherein the ventricles are not paced, the interval from a peak of the atrial depolarization to the end of atrial repolarization (i.e. $AS_{PEAK} - AT_{END}$) is measured. (As with example of FIG. 4, the peak of atrial depolarization event in FIG. 6 is identified as the first maxima within the event, not the overall maxima.) An offset is subtracted from the measured interval to yield the preferred the AS-VP pacing delay. The preferred AS-VP pacing delay is then applied during a next heartbeat 258 to time delivery of a V-pulse subsequent to the peak of the atrial depolarization of that heartbeat. By calculating the preferred/optimal the AS-VP pacing delay by subtracting the offset from $AS_{PEAK} - AT_{END}$, the V-pulse is thereby delivered prior to the end of the atrial T-wave (hence obscuring the end of the atrial T-wave.)

In general, the offset value is preferably set so as to time delivery of the V-pulse to be substantially contemporaneous with the atrial T-wave, i.e. the V-pulse is delivered at a point subsequent to the beginning of the atrial T-wave but before the end of the atrial T-wave. In the examples described herein, this is achieved by detecting the end of the atrial T-wave then subtracting the offset value. In other implementations, the beginning of the atrial T-wave is instead detected and then an offset value is added.

Returning to FIG. 5, the processing steps for use with paced atrial events will now be briefly summarized. Beginning at step 260, the implantable device identifies the peak of a paced atrial depolarization event ($AP_{PEAK}$) within the unipolar A-IEGM, i.e. the device detects the peak of the evoked response triggered by an A-pulse. At step 262, the end of the subsequent atrial repolarization event ($AT_{END}$) is then identified within the unipolar A-IEGM. In one example, a detection window is specified within the A-IEGM signal beginning 100 ms following the peak of the atrial depolarization event and extending to the end of the paced atrioventricular delay measured at step 232 of FIG. 3. The implanted device detects the atrial T-wave within that window then identifies the end of the atrial T-wave. At step 234, the preferred/optimal AP-VP delay is then determined by calculating:

$$AP\text{-}VP = AP_{PEAK} - AT_{END} - \text{offset}_{PACED}$$

where $\text{offset}_{PACED}$ is a predetermined offset value set, for example, within the range of 5 to 15 ms and, in one specific example, set to 10 ms. Otherwise routine experimentation may be performed for determining optimal values for offset-$_{PACED}$ that result in optimization of cardiac output and/or ventricular filling (or the least result in an improvement therein.) The preferred/optimal AP-VP delay value is then applied following subsequent paced atrial events to determine the time for delivering V-pulses to the ventricles.

Figure 7:
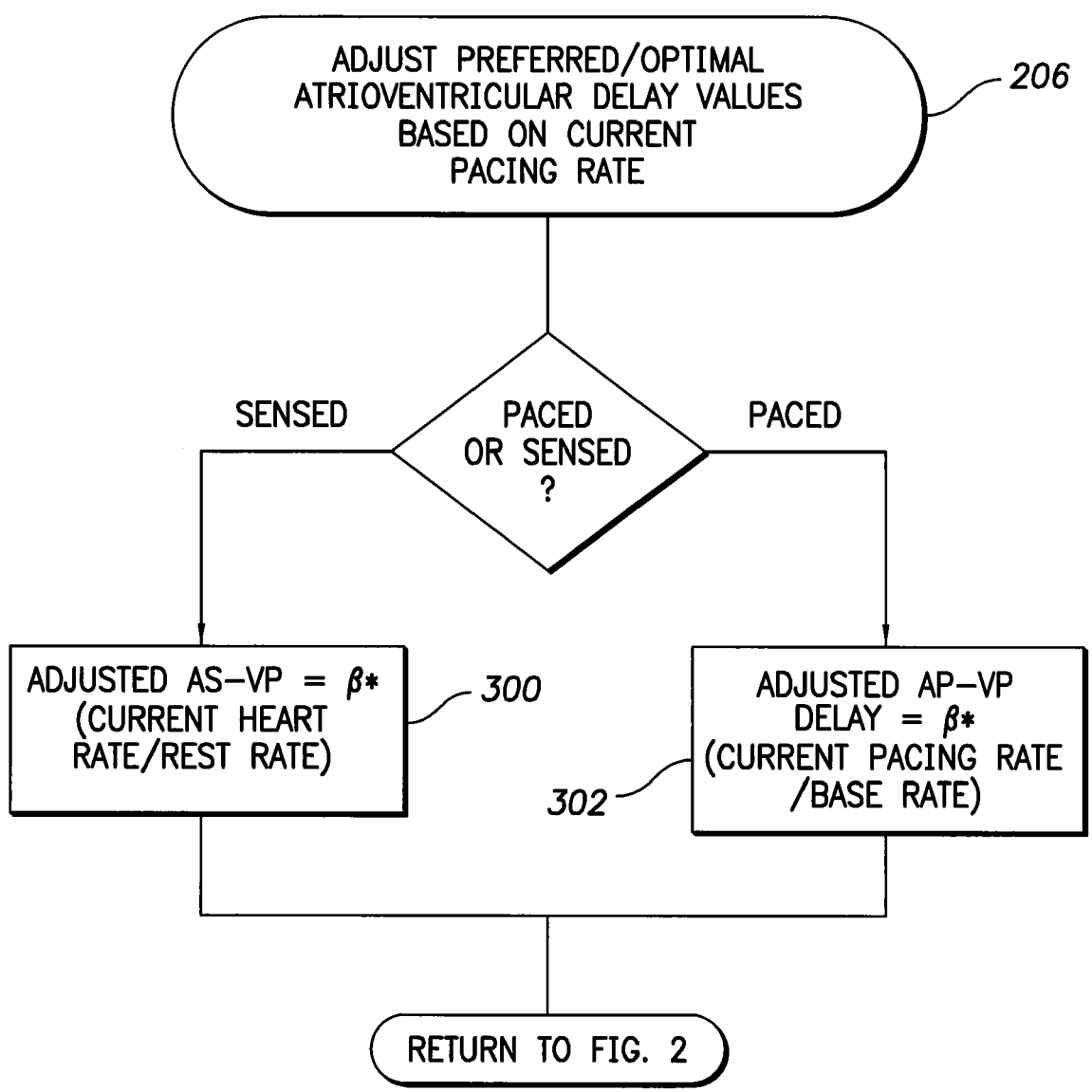
FIG. 7 is a flow chart illustrating an exemplary technique for adjusting atrioventricular delay values based on heart rate or pacing rate for use with the technique of FIG. 2.

Turning to the FIG. 7, an optional technique for adjusting the preferred/optimal atrioventricular pacing delay values for use at step 206 of FIG. 2 will now be described. Preferably, the optimal atrioventricular pacing delay values are more or less continuously detected and applied. Hence, if the heart rate changes, new optimal atrioventricular pacing delay values are automatically calculated at the new rate and hence no rate adjustment to the delay values is required. However, circumstances can arise when it is appropriate to apply delay values at a different rate than at rate at which they were initially obtained. For example, the ends of atrial repolarizations may be observable at a base/rest rate, but not at higher rates, thereby preventing optimal delay values from being directly calculated at the higher rates. If so, then it may be appropriate to rate adjust the optimal delay values that had been obtained at the base/rest rate for use at higher rates and FIG. 7 provides an appropriate rate adjustment technique. Again, the particular steps be performed depend upon whether atrial events are paced or sensed.

For sensed events, step 300 is performed, wherein the AS-VP pacing delay value is adjusted as follows:

$$\text{Rate Adjusted } AS\text{-}VP = \beta*(AS\text{-}VP)$$

where $\beta$=current heart rate/rest rate and AS-VP is an optimal atrioventricular delay initially calculated at rest rate.

Hence, AS-VP is adjusted based on the current intrinsic rate of the patient (which is monitored by the device using otherwise conventional techniques), in view of the intrinsic rest rate of the patient (which is periodically calculated by the device using otherwise conventional techniques.)

For paced events in atria, the AP-VP value is adjusted, at step 302, as follows:

$$\text{Rate Adjusted } AP\text{-}VP = \beta*(AP\text{-}VP)$$

where β=current pacing rate/base rate and AP-VP is an optimal atrioventricular delay initially calculated at base rate.

Thus, AP-VP is adjusted based on the current pacing rate of the patient, in view of the based pacing rate (which is set by the physician.)

Although rate adjustment has been described with respect to an example wherein the optimal delay values are initially obtained at rest/base rate, the general rate adjustment technique of FIG. 7 can be adapted to adjust delay values initially obtained at other, higher rates as well with appropriate selection of β.

What have been described thus far are various techniques for determining preferred or optimal AS-VP and AP-VP delay values for use by an implantable cardiac stimulation device. For the sake of completeness, detailed descriptions of an exemplary implantable cardiac stimulation device will now be described.

Exemplary Pacer/ICD

Figure 8:
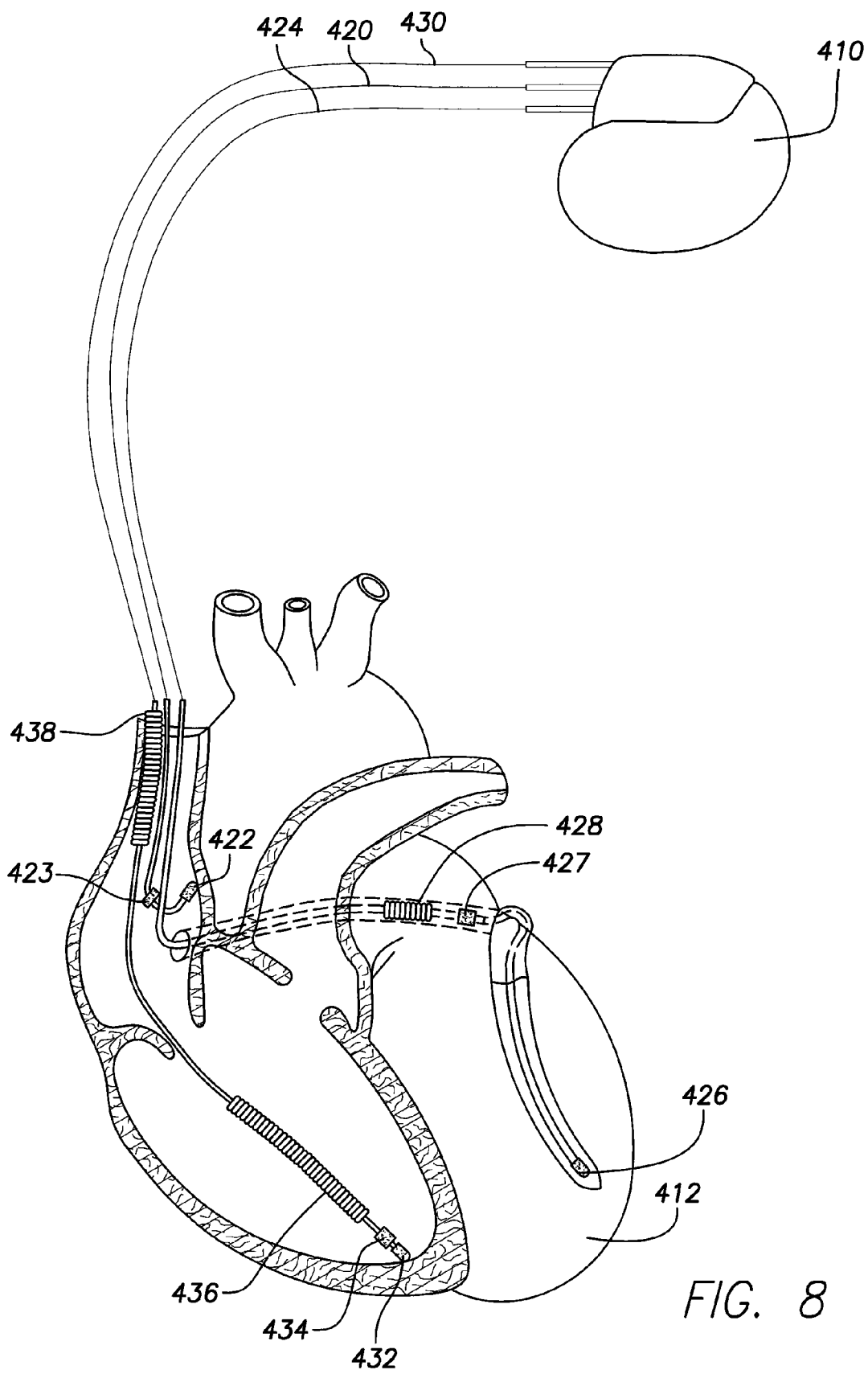
FIG. 8 is a simplified diagram illustrating an implantable stimulation device for use in implementing the techniques of FIGS. 1-7.
Figure 9:
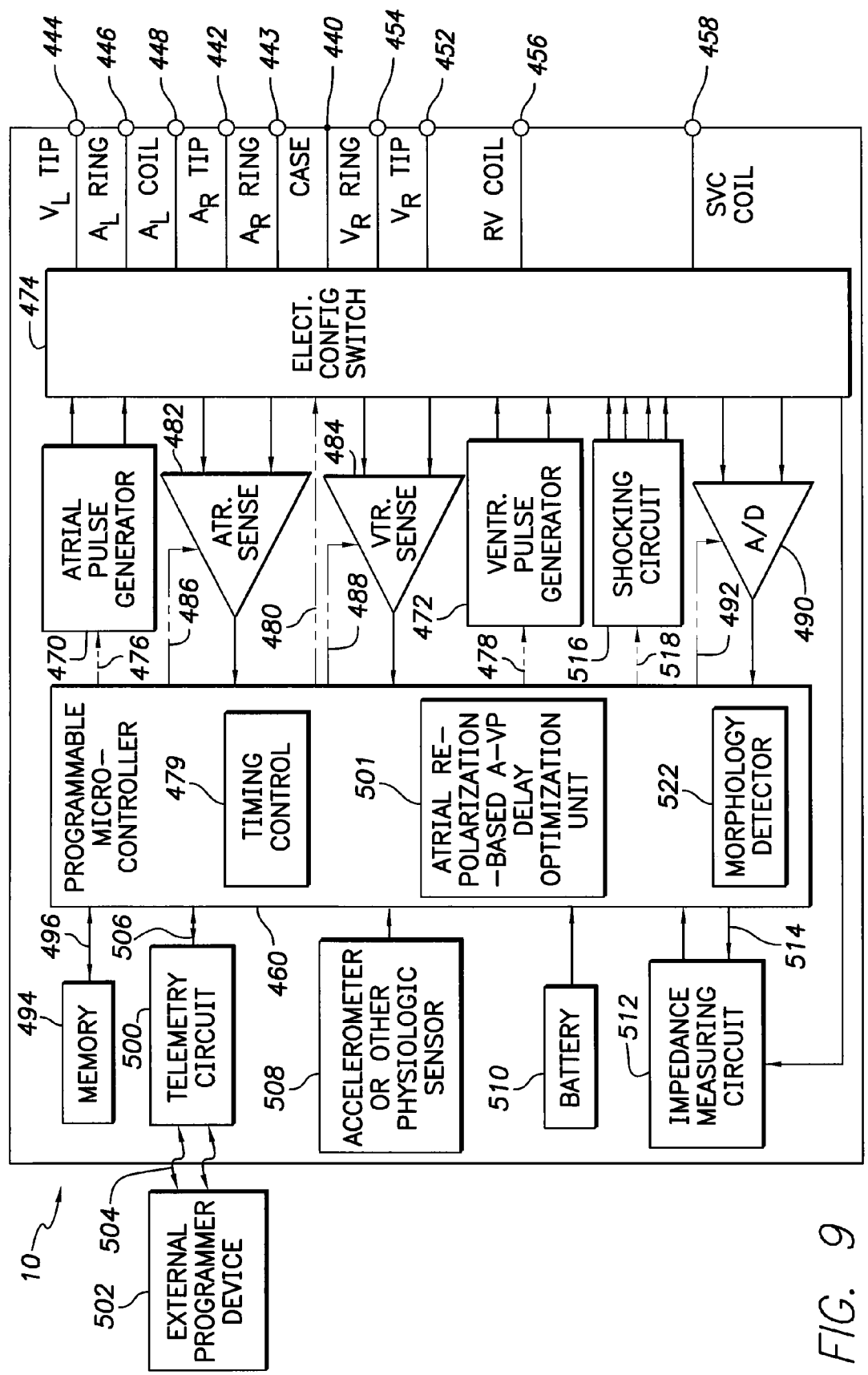
FIG. 9 is a functional block diagram primarily illustrating internal components of the implantable device of FIG. 11.

With reference to FIGS. 8 and 9, a description of an exemplary pacer/ICD will now be provided. FIG. 8 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart 412 by way of a left atrial lead 420 having an atrial tip electrode 422 and an atrial ring electrode 423 implanted in the atrial appendage. Pacer/ICD 410 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 8, it should also be understood that additional stimulation leads (with one or more pacing, sensing and/or shocking electrodes) might be used in order to efficiently and effectively provide pacing stimulation to the left side of the heart or atrial cardioversion and/or defibrillation.

A simplified block diagram of internal components of pacer/ICD 410 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 410, shown schematically in FIG. 9, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 9, an atrial pulse generator 470 and a ventricular pulse generator 472 generate pacing stimulation pulses for delivery by the right atrial lead 420, the right ventricular lead 430, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, atrioventricular delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, CS lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate ventricular tachycardia, high rate ventricular tachycardia, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 460 or memory 494) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AS-VP delay, AP-VP delay, V-V delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 9. The battery 510 may vary depending on the capabilities of pacer/ICD 410. If the system only provides low voltage therapy, a lithium iodine or lithium copper fluoride cell may be utilized. For pacer/ICD 410, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 410 is preferably capable of high voltage therapy and appropriate batteries.

As further shown in FIG. 9, pacer/ICD 410 is shown as having an impedance measuring circuit 512 which is enabled by the microcontroller 460 via a control signal 514. Thoracic impedance may be detected for use in tracking thoracic respiratory oscillations; lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 410 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with a VS event and/or pertaining to the treatment of tachycardia. Defibrillation shocks are generally of moderate to high energy level (i.e., corresponding to thresholds in the range of 5-40 joules), delivered asynchronously (since VS events may be too disorganized), and pertaining exclusively to the treatment of fibrillation. Accordingly, the microcontroller 460 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Insofar as atrioventricular pacing delay values are concerned, the microcontroller includes an on-board atrial repolarization-based A-VP delay optimization unit 501, which operates in accordance with techniques of FIGS. 1 and 7 to determine preferred or optimal AS-VP and AP-VP delay values based on IEGM signals.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for determining an atrioventricular pacing delay value for use in delivering cardiac pacing therapy to the heart of a patient in which an implantable cardiac stimulation device is implanted, said method comprising:
   determining a peak-to-peak interval between an atrial depolarization event and a ventricular depolarization event;
   comparing the interval to a minimum atrial repolarization detection threshold; and
   if the interval exceeds the threshold, detecting an atrial repolarization event; and determining an atrioventricular pacing delay value for use by the implantable cardiac stimulation device in pacing the heart of the patient based on the atrial repolarization event.

2. The method of claim 1 wherein determining a peak-to-peak interval between an atrial depolarization event and a ventricular depolarization event comprises:
   identifying a peak of a paced atrial depolarization event; and
   identifying a peak of an intrinsic ventricular depolarization event.

3. The method of claim 2 wherein the atrial depolarization event is identified within a unipolar atrial intracardiac electrogram (IEGM).

4. The method of claim 2 wherein the ventricular depolarization event is identified within a unipolar ventricular intracardiac electrogram (IEGM).

5. The method of claim 2 wherein the minimum atrial repolarization detection threshold comprises a paced atrial repolarization detection threshold around 260 ms.

6. The method of claim 1 wherein determining a peak-to-peak interval between an atrial depolarization event and a ventricular depolarization event comprises:
   identifying a peak of an intrinsic atrial depolarization event; and
   identifying a peak of an intrinsic ventricular depolarization event.

7. The method of claim 6 wherein the atrial depolarization event is identified within a unipolar atrial intracardiac electrogram (IEGM).

8. The method of claim 6 wherein the ventricular depolarization event is identified within a unipolar ventricular intracardiac electrogram (IEGM).

9. The method of claim 6 wherein the minimum atrial repolarization detection threshold comprises an intrinsic atrial repolarization detection threshold around 200 ms.

10. The method of claim 1 further comprising, if the interval does not exceed the threshold, determining an atrioventricular pacing delay value using a technique that does not involve atrial repolarization events.

11. A system for determining an atrioventricular pacing delay value for use in delivering cardiac pacing therapy to the heart of a patient in which an implantable cardiac stimulation device is implanted, the system comprising:
   an atrial event detector operative to detect atrial events within an atrial intracardiac electrogram signal;
   a ventricular event detector operative to detect ventricular events within ventricular intracardiac electrogram signal;
   a processor operative to:
      determine a peak-to-peak interval between an atrial depolarization event and a ventricular depolarization event;

compare the interval to a minimum atrial repolarization detection threshold; and if the interval exceeds the threshold, detect an atrial repolarization event; and determine an atrioventricular pacing delay value for use by the implantable cardiac stimulation device in pacing the heart of the patient based on the atrial repolarization event.

12. The system of claim 11 further comprising a plurality of electrodes and a switch, wherein the processor is operative to control the switch to create a unipolar electrode configuration for providing the atrial intracardiac electrogram signal.

13. The system of claim 11 further comprising a plurality of electrodes and a switch, wherein the processor is operative to control the switch to create a unipolar electrode configuration for providing the ventricular intracardiac electrogram signal.

14. A system for determining an atrioventricular pacing delay value for use in delivering cardiac pacing therapy to the heart of a patient in which an implantable cardiac stimulation device is implanted, the system comprising:

means for determining a peak-to-peak interval between an atrial depolarization event and a ventricular depolarization event;

means for comparing the interval to a minimum atrial repolarization detection threshold; and means for, if the interval exceeds the threshold, detecting an atrial repolarization event; and determining an atrioventricular pacing delay value for use by the implantable cardiac stimulation device in pacing the heart of the patient based on the atrial repolarization event.

* * * * *